(12) United States Patent
Payton et al.

(10) Patent No.: US 11,458,273 B2
(45) Date of Patent: Oct. 4, 2022

(54) APPARATUS FOR MEASURING PROPERTIES OF GASES SUPPLIED TO A PATIENT

(71) Applicant: Fisher & Paykel Healthcare Limited, Auckland (NZ)

(72) Inventors: Matthew Jon Payton, Auckland (NZ); Kevin Peter O'Donnell, Auckland (NZ); Andrew Baden Clark, Auckland (NZ); Christopher Simon James Quill, Auckland (NZ); Peter Geoffrey Hawkins, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 17/734,884

(22) Filed: May 2, 2022

(65) Prior Publication Data

US 2022/0257896 A1     Aug. 18, 2022

Related U.S. Application Data

(63) Continuation of application No. 17/240,155, filed on Apr. 26, 2021, which is a continuation of application
(Continued)

(30) Foreign Application Priority Data

Aug. 20, 2004   (NZ) ........................................ 534853

(51) Int. Cl.
*A61M 16/00* (2006.01)
*A61M 16/10* (2006.01)
(Continued)

(52) U.S. Cl.
CPC .... *A61M 16/1005* (2014.02); *A61M 16/0066* (2013.01); *A61M 16/024* (2017.08);
(Continued)

(58) Field of Classification Search
CPC ............ A61M 16/1005; A61M 16/109; A61M 16/1095; A61M 16/161; A61M 16/024;
(Continued)

(56) References Cited

U.S. PATENT DOCUMENTS 485,127 A    10/1892  Lynch
3,243,753 A   3/1966  Kohler
(Continued)

FOREIGN PATENT DOCUMENTS

CN    1370085    9/2002
DE    3311811   10/1984
(Continued)

OTHER PUBLICATIONS

Letter transmitting Examiner's Report in Canadian Application No. 2576409, dated Mar. 31, 2011, in 2 pages.
(Continued)

*Primary Examiner* — Steven O Douglas
(74) *Attorney, Agent, or Firm* — Knobbe, Martens, Olson & Bear, LLP

(57) ABSTRACT

The gases temperature supplied to a patient when the patient is undergoing treatment such as oxygen therapy or positive pressure treatment for conditions such as Obstructive Sleep Apnea (OSA) or Chronic Obstructive Pulmonary Disease (COPD) is often measured for safety and to enable controlling of the humidity delivered to the patient. The invention disclosed is related to measurement of properties, particularly temperature (thermistor), of gases flowing through a heated tube, supplying gases to a patient, which utilises the heating wire within the tube.

28 Claims, 4 Drawing Sheets

Related U.S. Application Data

No. 16/714,311, filed on Dec. 13, 2019, now Pat. No. 11,007,340, which is a continuation of application No. 15/010,321, filed on Jan. 29, 2016, now Pat. No. 10,537,698, which is a continuation of application No. 13/908,952, filed on Jun. 3, 2013, now Pat. No. 9,265,902, which is a continuation of application No. 11/572,822, filed as application No. PCT/NZ2005/000219 on Aug. 19, 2005, now Pat. No. 8,453,641.

(51) Int. Cl.
*A61M 16/16* (2006.01)
*A61M 16/06* (2006.01)
*A61M 16/08* (2006.01)

(52) U.S. Cl.
CPC ........ *A61M 16/06* (2013.01); *A61M 16/0666* (2013.01); *A61M 16/0875* (2013.01); *A61M 16/109* (2014.02); *A61M 16/1075* (2013.01); *A61M 16/1095* (2014.02); *A61M 16/16* (2013.01); *A61M 16/161* (2014.02); *A61M 2016/0027* (2013.01); *A61M 2016/102* (2013.01); *A61M 2205/3368* (2013.01); *A61M 2205/502* (2013.01); *Y10S 261/65* (2013.01)

(58) Field of Classification Search
CPC .............. A61M 16/0066; A61M 16/06; A61M 16/0666; A61M 16/0875; A61M 16/1075; A61M 16/16; A61M 2016/0027; A61M 2016/102; A61M 2205/3368; A61M 2205/502; Y10S 261/65
See application file for complete search history.

(56) References Cited

U.S. PATENT DOCUMENTS

| | | |
|---|---|---|
| 3,582,968 A | 6/1971 | Buiting |
| 3,584,193 A | 6/1971 | Badertscher |
| 3,638,926 A | 2/1972 | Melville et al. |
| 3,695,267 A | 10/1972 | Hirtz et al. |
| 3,766,914 A | 10/1973 | Jacobs |
| 3,823,217 A | 7/1974 | Kampe |
| 3,903,883 A | 9/1975 | Pecina et al. |
| 3,913,379 A | 10/1975 | Rusz et al. |
| 3,914,349 A | 10/1975 | Stipanuk |
| 4,013,122 A | 3/1977 | Long |
| 4,013,742 A | 3/1977 | Lang |
| 4,038,980 A | 8/1977 | Fodor |
| 4,050,823 A | 9/1977 | Frankenberger |
| 4,051,205 A | 9/1977 | Grant |
| 4,060,576 A | 11/1977 | Grant |
| 4,110,419 A | 8/1978 | Miller |
| 4,152,379 A | 5/1979 | Suhr |
| 4,162,370 A | 7/1979 | Dunn et al. |
| 4,172,105 A | 10/1979 | Miller et al. |
| D253,409 S | 11/1979 | Voelkert |
| 4,177,376 A | 12/1979 | Horsma et al. |
| 4,203,027 A | 5/1980 | O'Hare et al. |
| 4,459,473 A | 7/1984 | Kamath |
| 4,500,480 A | 2/1985 | Cambio, Jr. |
| 4,529,867 A | 7/1985 | Velnosky et al. |
| 4,532,088 A | 7/1985 | Miller |
| 4,543,474 A | 9/1985 | Horsma et al. |
| 4,560,498 A | 12/1985 | Horsma et al. |
| 4,574,188 A | 3/1986 | Midgley et al. |
| 4,621,632 A | 11/1986 | Bartels et al. |
| 4,639,055 A | 1/1987 | Keane |
| 4,640,804 A | 2/1987 | Mizoguchi |
| 4,676,237 A | 6/1987 | Wood et al. |
| 4,682,010 A | 7/1987 | Drapeau et al. |
| 4,684,786 A | 8/1987 | Mann et al. |
| 4,686,354 A | 8/1987 | Makin |
| 4,695,955 A | 9/1987 | Faisandier |
| 4,708,831 A | 11/1987 | Elsworth et al. |
| 4,710,887 A | 12/1987 | Ho |
| 4,715,998 A | 12/1987 | Clow |
| 4,722,334 A | 2/1988 | Blackmer et al. |
| 4,736,090 A | 4/1988 | De Broechk et al. |
| 4,753,758 A | 6/1988 | Miller |
| 4,780,247 A | 10/1988 | Yasuda |
| 4,787,117 A | 11/1988 | Westergren |
| 4,791,966 A | 12/1988 | Eilentropp |
| 4,807,616 A | 2/1989 | Adahan |
| 4,808,793 A | 2/1989 | Hurko |
| 4,826,444 A | 5/1989 | Genoa et al. |
| 4,829,781 A | 5/1989 | Hitzier |
| 4,829,998 A | 5/1989 | Jackson |
| 4,911,157 A | 3/1990 | Miller |
| 4,911,357 A | 3/1990 | Kitamura |
| 4,921,642 A | 5/1990 | LaTorraca |
| 4,941,469 A | 7/1990 | Adahan |
| 4,955,372 A | 9/1990 | Blackmer et al. |
| D313,969 S | 1/1991 | Lacroix |
| 5,031,612 A | 7/1991 | Clementi |
| 5,062,145 A | 10/1991 | Zwaan et al. |
| 5,092,326 A | 3/1992 | Winn et al. |
| 5,101,820 A | 4/1992 | Christopher |
| 5,121,746 A | 6/1992 | Sikora |
| 5,148,801 A | 9/1992 | Douwens et al. |
| 5,164,652 A | 11/1992 | Johnson et al. |
| 5,203,343 A | 4/1993 | Axe et al. |
| 5,224,923 A | 7/1993 | Moffett et al. |
| 5,230,331 A | 7/1993 | Rusz et al. |
| 5,231,979 A | 8/1993 | Rose et al. |
| 5,336,156 A | 8/1994 | Miller et al. |
| 5,346,128 A | 9/1994 | Wacker |
| 5,347,211 A | 9/1994 | Jakubowski |
| 5,367,604 A | 11/1994 | Murray |
| 5,387,117 A | 2/1995 | Moyher, Jr. et al. |
| 5,388,443 A | 2/1995 | Manaka |
| 5,392,770 A | 2/1995 | Clawson et al. |
| 5,404,729 A | 4/1995 | Matsuoka et al. |
| 5,428,752 A | 6/1995 | Goren |
| D362,718 S | 9/1995 | Deily et al. |
| 5,449,234 A | 9/1995 | Gipp et al. |
| 5,454,061 A | 9/1995 | Carlson |
| 5,482,031 A | 1/1996 | Lambert |
| 5,492,676 A | 2/1996 | Katatani et al. |
| 5,516,466 A | 5/1996 | Schlesch et al. |
| 5,529,060 A | 6/1996 | Salmon et al. |
| 5,537,996 A | 7/1996 | McPhee |
| 5,537,997 A | 7/1996 | Mechlenburg et al. |
| 5,551,419 A | 9/1996 | Froehlich |
| 5,558,084 A | 9/1996 | Daniell et al. |
| 5,564,415 A | 10/1996 | Dobson et al. |
| 5,588,423 A | 12/1996 | Smith |
| 5,600,752 A | 2/1997 | Lopatinsky |
| 5,637,006 A | 6/1997 | Almeras |
| 5,640,951 A | 6/1997 | Huddart et al. |
| 5,658,159 A | 8/1997 | Gardner et al. |
| 5,662,101 A | 9/1997 | Ogden et al. |
| 5,673,687 A | 10/1997 | Dobson et al. |
| 5,705,555 A | 1/1998 | Guilfoy et al. |
| 5,759,149 A | 6/1998 | Goldberg et al. |
| 5,769,071 A | 6/1998 | Turnbull |
| 5,778,872 A | 7/1998 | Fukunaga et al. |
| 5,906,201 A | 5/1999 | Nilson |
| 5,916,493 A | 6/1999 | Miller |
| 5,943,473 A | 8/1999 | Levine |
| 5,980,289 A | 11/1999 | Engle |
| 5,988,164 A | 11/1999 | Paluch |
| 5,991,507 A | 11/1999 | Bencsits |
| 6,024,694 A | 2/2000 | Goldberg et al. |
| 6,038,457 A | 3/2000 | Barkat |
| 6,050,260 A | 4/2000 | Daniell et al. |
| 6,078,730 A | 6/2000 | Huddart et al. |
| 6,090,313 A | 7/2000 | Zhao |
| 6,095,505 A | 8/2000 | Miller |
| 6,109,782 A | 8/2000 | Fukura et al. |
| 6,125,847 A | 10/2000 | Lin |
| 6,158,431 A | 12/2000 | Poole |
| 6,167,883 B1 | 1/2001 | Beran et al. |

(56) References Cited

U.S. PATENT DOCUMENTS

| | | |
|---|---|---|
| 6,189,870 B1 | 2/2001 | Withall |
| 6,238,598 B1 | 5/2001 | Chen |
| 6,240,921 B1 | 6/2001 | Brydon et al. |
| 6,256,454 B1 | 7/2001 | Dykes |
| 6,272,933 B1 | 8/2001 | Gradon et al. |
| 6,311,958 B1 | 11/2001 | Stanek |
| 6,349,722 B1 | 2/2002 | Gradon et al. |
| 6,360,741 B2 | 3/2002 | Trushel |
| 6,367,472 B1 | 4/2002 | Koch |
| 6,384,755 B1 | 5/2002 | Hayden |
| 6,394,084 B1 | 5/2002 | Nitta |
| 6,397,841 B1 | 6/2002 | Kenyon et al. |
| 6,397,846 B1 | 6/2002 | Skog et al. |
| 6,398,197 B1 | 6/2002 | Dickinson et al. |
| 6,412,488 B1 | 7/2002 | Barnett et al. |
| 6,435,180 B1 | 8/2002 | Hewson et al. |
| 6,440,512 B1 | 8/2002 | Thomas et al. |
| 6,463,925 B2 | 10/2002 | Nuckols et al. |
| 6,464,520 B2 | 10/2002 | Saba |
| 6,474,335 B1 | 11/2002 | Lammers |
| 6,536,432 B2 | 3/2003 | Trushel |
| D472,970 S | 4/2003 | Lund |
| 6,543,412 B2 | 4/2003 | Amou et al. |
| 6,564,011 B1 | 5/2003 | Janoff et al. |
| 6,584,972 B2 | 7/2003 | McPhee |
| 6,594,366 B1 | 7/2003 | Adams |
| 6,668,828 B1 | 12/2003 | Figley et al. |
| 6,694,974 B1 | 2/2004 | George-Gradon et al. |
| 6,705,478 B1 | 3/2004 | Engle |
| 6,718,974 B1 | 4/2004 | Moberg |
| 6,773,138 B2 | 8/2004 | Coushaine |
| 6,796,308 B2 | 9/2004 | Gunatatnam et al. |
| 6,816,669 B2 | 11/2004 | Zimmer et al. |
| 6,851,425 B2 | 2/2005 | Jaffre et al. |
| 6,918,389 B2 | 7/2005 | Seakins et al. |
| 6,953,354 B2 | 10/2005 | Edirisuriya et al. |
| 7,096,864 B1 | 8/2006 | Mayer et al. |
| 7,111,624 B2 | 9/2006 | Thudor et al. |
| 7,120,354 B2 | 10/2006 | Mackie et al. |
| 7,131,842 B2 | 11/2006 | Hollingsworth et al. |
| 7,140,367 B2 | 11/2006 | White et al. |
| 7,146,979 B2 | 12/2006 | Seakins et al. |
| 7,327,949 B1 | 2/2008 | Cheng et al. |
| 7,364,140 B2 | 4/2008 | Lipscombe et al. |
| 7,453,043 B2 | 11/2008 | Park et al. |
| 7,468,116 B2 | 12/2008 | Smith et al. |
| 7,588,029 B2 | 9/2009 | Smith et al. |
| 7,588,186 B2 | 9/2009 | Steffen et al. |
| D619,964 S | 7/2010 | Coushaine et al. |
| 7,766,050 B2 | 8/2010 | Patel |
| D627,296 S | 11/2010 | Vogt et al. |
| D628,288 S | 11/2010 | Row et al. |
| 7,827,990 B1 | 11/2010 | Melidis et al. |
| D634,015 S | 3/2011 | King et al. |
| 7,933,780 B2 | 4/2011 | De La Huerga |
| 7,987,847 B2 | 8/2011 | Wickham |
| 8,063,343 B2 | 11/2011 | McGhin et al. |
| D650,741 S | 12/2011 | Sun et al. |
| 8,069,854 B2 | 12/2011 | Colla et al. |
| 8,091,547 B2 | 1/2012 | Thudor et al. |
| 8,122,882 B2 | 2/2012 | McGhin et al. |
| D660,960 S | 5/2012 | Grönberg |
| 8,186,345 B2 | 5/2012 | Payton et al. |
| 8,235,041 B2 | 8/2012 | Seakins et al. |
| 8,245,710 B2 | 8/2012 | Makinson et al. |
| 8,316,848 B2 | 11/2012 | Kowk et al. |
| 8,453,641 B2 | 6/2013 | Payton et al. |
| D689,436 S | 9/2013 | Sun et al. |
| 8,550,072 B2 | 10/2013 | Thudor et al. |
| 8,550,084 B2 | 10/2013 | Ng et al. |
| 9,265,902 B2 | 2/2016 | Payton et al. |
| 9,555,210 B2 | 1/2017 | Seakins et al. |
| 9,750,917 B2 | 9/2017 | Seakins et al. |
| 9,814,856 B2 | 11/2017 | Payton et al. |
| 10,398,861 B2 | 9/2019 | O'Donnell et al. |
| 10,525,225 B2 | 1/2020 | Seakins et al. |
| 10,537,698 B2 | 1/2020 | Payton et al. |
| 10,709,865 B2 | 7/2020 | Payton et al. |
| 11,007,340 B2 | 5/2021 | Payton et al. |
| 2001/0004894 A1 | 6/2001 | Bourdon |
| 2001/0017134 A1 | 8/2001 | Bahr |
| 2002/0020416 A1 | 2/2002 | Namey |
| 2002/0038392 A1 | 3/2002 | De La Huerga |
| 2002/0083947 A1 | 7/2002 | Seakins |
| 2002/0186966 A1 | 12/2002 | Zimmer et al. |
| 2003/0079748 A1 | 5/2003 | Seakins |
| 2003/0111079 A1 | 6/2003 | Matthews et al. |
| 2003/0154977 A1 | 8/2003 | White et al. |
| 2004/0074495 A1 | 4/2004 | Wickham et al. |
| 2004/0118406 A1 | 6/2004 | Lithgow et al. |
| 2004/0149284 A1 | 8/2004 | Smith et al. |
| 2004/0163648 A1 | 8/2004 | Burton |
| 2004/0182392 A1 | 9/2004 | Gerder et al. |
| 2005/0053908 A1 | 3/2005 | Satheesh et al. |
| 2005/0076906 A1 | 4/2005 | Johnson |
| 2005/0152733 A1 | 7/2005 | Patel |
| 2005/0155604 A1 | 7/2005 | Ging et al. |
| 2006/0086357 A1 | 4/2006 | Soliman et al. |
| 2006/0278221 A1 | 12/2006 | Schermeier et al. |
| 2007/0044804 A1 | 3/2007 | Matual et al. |
| 2007/0221224 A1 | 9/2007 | Pittman et al. |
| 2008/0251071 A1 | 10/2008 | Armitsread et al. |
| 2008/0295837 A1 | 12/2008 | McCormick et al. |
| 2009/0035733 A1 | 2/2009 | Meitar et al. |
| 2009/0110379 A1 | 4/2009 | McGhin et al. |
| 2009/0199850 A1 | 8/2009 | Colla et al. |
| 2009/0293875 A1 | 12/2009 | Kwok et al. |
| 2009/0320840 A1 | 12/2009 | Klasek et al. |
| 2010/0010477 A1 | 1/2010 | Augustine et al. |
| 2010/0190143 A1 | 7/2010 | Gal et al. |
| 2010/0291528 A1 | 11/2010 | Huerta |
| 2011/0167013 A1 | 7/2011 | Pogue et al. |
| 2012/0125333 A1 | 5/2012 | Bedford et al. |
| 2012/0247470 A1 | 10/2012 | Ho et al. |
| 2013/0312750 A1 | 11/2013 | Farrugla et al. |
| 2014/0283831 A1 | 9/2014 | Foote et al. |
| 2014/0311487 A1 | 10/2014 | Buechi et al. |
| 2019/0336711 A1 | 11/2019 | O'Donnell et al. |
| 2022/0040435 A1 | 2/2022 | Payton et al. |

FOREIGN PATENT DOCUMENTS

| | | |
|---|---|---|
| DE | 3629353 | 1/1988 |
| DE | 4020522 A1 | 1/1992 |
| DE | 4034611 | 5/1992 |
| DE | 4102223 A1 | 7/1992 |
| DE | 9409231.1 | 12/1994 |
| DE | 19647548 A1 | 5/1998 |
| DE | 19725875 A1 | 12/1998 |
| DE | 19958296 C1 | 9/2001 |
| DE | 20202906 U1 | 2/2002 |
| DE | 10312881 B3 | 5/2004 |
| DE | 202006007397 U1 | 9/2007 |
| DE | 102007003454 A1 | 7/2008 |
| DE | 102007003455 A1 | 8/2008 |
| EP | 0258928 | 9/1988 |
| EP | 0356000 | 2/1990 |
| EP | 0481459 | 4/1992 |
| EP | 0556561 | 8/1993 |
| EP | 0616166 | 9/1994 |
| EP | 0672430 | 9/1995 |
| EP | 0885623 | 12/1998 |
| EP | 0661071 B1 | 2/2000 |
| EP | 1127583 A2 | 8/2001 |
| EP | 1138341 | 10/2001 |
| EP | 1166814 A2 | 1/2002 |
| EP | 1145678 A2 | 4/2002 |
| EP | 1579884 A1 | 9/2005 |
| EP | 1778330 A1 | 5/2007 |
| GB | 1167551 | 10/1969 |
| GB | 1448473 | 9/1976 |
| GB | 2056611 A | 3/1981 |
| GB | 2173274 A | 10/1986 |
| GB | 2 277 689 | 11/1994 |

(56) References Cited

FOREIGN PATENT DOCUMENTS

| | | |
|---|---|---|
| JP | S53-043943 | 4/1978 |
| JP | S61-294479 | 12/1986 |
| JP | S62-26076 | 2/1987 |
| JP | H02-193680 | 7/1990 |
| JP | H02-118555 U | 9/1990 |
| JP | H04-200477 | 7/1992 |
| JP | 05-317428 | 12/1993 |
| JP | H07-16955 U | 3/1995 |
| JP | H07-204273 | 8/1995 |
| JP | 08-061731 | 3/1996 |
| JP | H08-317428 | 11/1996 |
| JP | 09-234247 | 9/1997 |
| JP | H09-276408 | 10/1997 |
| JP | H10-028737 | 2/1998 |
| JP | H10-506544 | 6/1998 |
| JP | H11-057009 | 3/1999 |
| JP | 2000-024109 | 1/2000 |
| JP | 2000-167055 | 6/2000 |
| JP | 2001-129091 | 5/2001 |
| JP | 2002-272849 | 9/2002 |
| JP | 2002-291655 | 10/2002 |
| JP | 2003-516825 | 5/2003 |
| JP | 3475261 | 12/2003 |
| SU | 379270 | 4/1973 |
| WO | WO 92/21163 | 11/1992 |
| WO | WO 96/000528 | 1/1996 |
| WO | WO 97/18001 A1 | 5/1997 |
| WO | WO 98/04311 A1 | 2/1998 |
| WO | WO 98/26826 | 6/1998 |
| WO | WO 01/10489 | 2/2001 |
| WO | WO 02/32486 A1 | 4/2002 |
| WO | WO 02/066106 A1 | 8/2002 |
| WO | WO 03/018096 | 3/2003 |
| WO | WO 2004/011072 | 2/2004 |
| WO | WO 2004/105848 | 12/2004 |
| WO | WO 2005/021076 | 3/2005 |
| WO | WO 2006/019323 | 2/2006 |
| WO | WO 2006/092001 | 9/2006 |
| WO | WO 2006/133494 A1 | 12/2006 |
| WO | WO 2008/055308 | 5/2008 |
| WO | WO 2012/012835 A2 | 2/2012 |
| WO | WO 2012/020314 A2 | 2/2012 |
| WO | WO 2014/077706 A1 | 5/2014 |
| WO | WO 2015/038013 A1 | 3/2015 |

OTHER PUBLICATIONS

Examiner's Report in Canadian Application No. 2576409, dated Nov. 1, 2012, by Dan Rempel, in 2 pages.
Examination Search Report for Canadian Patent Application No. 2,850,679, dated Nov. 25, 2016 in 3 pages.
Office Action issued in Canadian Patent Application No. 2,850,679, dated Dec. 11, 2017, in 3 pages.
Office Action issued in Canadian Patent Application No. 2,850,679, dated Mar. 6, 2019, in 4 pages.
Office Action issued in Canadian Patent Application No. 2,871,850 dated Mar. 12, 2020, in 4 pages.
Chinese Examination Report of CN Application No. 200580028386.6, cover letters dated Jul. 19, 2011 and dated Aug. 12, 2011, with English translation of pertinent portions of examination report.
Chinese Examination Report of CN Application No. 200580028386.6, with English translation of pertinent portion, dated Apr. 12, 2012, in 8 pages.
Office Action issued in Chinese Patent Application No. 201310020628.3, dated Oct. 19, 2015, in 3 pages.
Reexamination Translation for related Chinese Patent Application No. 201310020628.3, Apr. 12, 2017 in 6 pages.
European Search Report issued in European Patent Application No. 03012599.1, dated Oct. 20, 2003, in 5 pages.
Supplemental European Search Report issued in European Patent Application No. EP 03797756.8, dated Feb. 18, 2013, in 6 pages.
Supplementary Partial European Search Report for EP Application No. 05776618.0, dated May 29, 2017 in 10 pages.
Examination Report issued in European Patent Application No. 05776618.0, dated Dec. 19, 2018, in 7 pages.
Examination Report issued in European Patent Application No. 05776618.0, dated Jul. 24, 2019, in 7 pages.
Examination Report issued in Japanese Patent Application No. 2011-266229, dated Feb. 7, 2013, in 2 pages.
JP Examination Report; JP2012-020278; dated Feb. 3, 2015, 4 pages.
JP Examination Report; JP2013-168353; dated Jun. 24, 2014; 6 pages.
JP Examination Report; JP2013-168354; dated Jun. 24, 2014; 5 pages.
Office Action dated Aug. 2, 2016 issued in Japanese Application No. 2015-212046, along with its English translation, in 20 pages.
English Translation of Notice of Reasons for Rejection for related Japanese Patent Application No. 2015-212046, dated Aug. 1, 2017 in 4 pages.
International Search Report received in PCT Application No. PCT/NZ2005/000219, dated Sep. 28, 2005.
Extended European Search Report for PCT/NZ2005/000219 dated Jun. 7, 2017 in 10 pages.
International Search Report received in PCT Application No. PCT/NZ2013/000088, dated Aug. 9, 2013.
Written Opinion of the ISA received in PCT Application No. PCT/NZ2013/000088, dated Aug. 9, 2014.
Patent Owner's Complaint for *Fisher & Paykel Healthcare Ltd.* v. *ResMed Corp.*, Case No. 3:16-cv-02068-GPC-WVG (S.D. Cal.) dated Aug. 16, 2016, in 29 pages.
Petitioners' Complaint for *ResMed Inc., et al.* v. *Fisher & Paykel Healthcare Corp. Ltd., et al.*, Case No. 3:16-cv-02072-JAH-MDD (S.D. Cal.) dated Aug. 16, 2016, in 65 pages.
Petitioners' Notice of Voluntary Dismissal Without Prejudice for *ResMed Inc., et al.* v. *Fisher & Paykel Healthcare Corp. Ltd., et al.*, Case No. 3:16-cv-02072-JAH-MDD (S.D. Cal.) dated Aug. 18, 2016, in 3 pages.
Patent Owner's Complaint for *Fisher & Paykel Healthcare Ltd.* v. *ResMed Corp.*, Case No. 2:16-cv-06099-R-AJW (C.D. Cal.) dated Aug. 15, 2016, in 29 pages.
Patent Owner's Notice of Voluntary Dismissal Without Prejudice for *Fisher & Paykel Healthcare Ltd.* v. *ResMed Corp.*, Case No. 2:16-cv-06099-R-AJW (C.D. Cal.) dated Aug. 16, 2016, in 2 pages.
Second Declaration of *Andrew Bath, ResMed Inc., ResMed Corp, and ResMed Limited* v. *Fisher & Paykel Healthcare Limited*, Case No. IPR2016-01724, dated Aug. 24, 2017, in 40 pages.
Second Declaration of *Andrew Bath, ResMed Inc., ResMed Corp, and ResMed Limited* v. *Fisher & Paykel Healthcare Limited*, Case No. IPR2016-01735, dated Aug. 24, 2017, in 37 pages.
Bobrow, Leonard S., Elementary Linear Circuit Analysis, Second Edition, ISBN: 0-03-007298-0, CBD College Publishing, 1987, pp. 168-169, 222-223, 236-237, 266-267, 350-351 in 7 pages.
Effect of Polyethylene on Morphology and Dielectric Breakdown in EVA Blends from http://ieeexplore.ieee.org; One (1) page; Issued date Jul. 8-13, 2007, paper appears in Solid Dielectrics, 2007 ICSD '07. IEEE International Conference.
Fisher & Paykel Healthcare, Annual Report 2003, accessed from https://www.fphcare.co.nz/files/documents/investorannouncements/annual-interim-reports-_-en/ar2003_full/.
Fisher & Paykel Healthcare, FY04 Full Year Overview & Update, May 24, 2004, dated on https://www.fphcare.com/investor/presentations/presentations-2004/, accessed from https://www.fphcare.com/CMSPages/GetFile.aspx?guid=50c66a57-cb04-4e4d-b220-92e371d07292.
Fisher & Paykel Healthcare, Full Year Analyst Briefing, Jun. 5, 2002, dated on https://www.fphcare.com/investor/presentations/presentations-2002/, accessed from https://www.fphcare.com/CMSPages/GetFile.aspx?guid=ef7b02d1-cc43-4d62-a1f7-494be1bbb2dc.
Fisher & Paykel Healthcare, MR810 Respiratory Humidifier Technical Manual Revision C, 2004, Fisher & Paykel Healthcare Ltd, Auckland, New Zealand, 43 pages.

(56) References Cited

OTHER PUBLICATIONS

Fisher & Paykel Healthcare, MR850 Respiratory Humidifier Instruction Sheet, Rev. G, Feb. 2004 ("MR850 Instruction Sheet").
Frenzel, Louise E. Jr., Crash Course in Electronics Technology, Second Edition, ISBN: 0-7506-9710-5, 1996, pp. 1-6.
Horowitz et al., The Art of Electronics, Cambridge University Press 1980, 1989, ISBN: 0-521-37095-7, pp. 48-52, 116, in 6 pages.
IEEE 100 The Authoritive Dictionary of IEEE Standards Terms, Seventh Edition, The Definition of Resistor, The Institute of Electrical and Electronics Engineers, Inc., p. 972, dated Dec. 2000, in 3 pages.
Khandpurk, Dr. R.S., Printed Circuit Boards, Design, Fabrication, Assembly and Testing, ISBN: 0-07-146420-4, Glossary, McGraw-Hill 2006, in 5 pages.
Phillips, Geoff, Newnes Electronics Toolkit, ISBN: 075060929 X, 1993, p. 25, in 4 pages.
Potter, "Measuring Temperature with Thermistors—a Tutorial" Thermistors—National Instruments Application Note 065, National Instruments Corporation, Nov. 1996, pp. 1-8.
Printout from www.astm.org/Standards/D1351.htm of ASTM D1351-08 Standard Specification for Thermoplastic Polyethylene Insulation for Electrical Wire and Cable; Two (2) pages; Copyright 1996-2010 (051CP1DV1).
Shiva, Sajjan G., "Hardware Technologies" Introduction to Logic Design, Second Edition, ISBN: 0-8247-0082-1, 1998, p. 495, in 4 pages.
Vishay BCcomponents, 2322 640 3/4/6, "NTC Thermistors, Accuracy Line" from www.vishay.com, Oct. 10, 2003 in 19 pages.

APPARATUS FOR MEASURING PROPERTIES OF GASES SUPPLIED TO A PATIENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

This invention relates to an apparatus for measuring properties, such as temperature and humidity, of gases being supplied to a patient. Humidifiers are commonly controlled by measuring the temperature of gas at two points, adjacent to the output of the humidifier and proximal to the patient. This invention predominantly relates to the measurement of temperature of gas supplied to a patient at a point proximal to the patient.

Description of the Related Art

The gases temperature supplied to a patient when the patient is undergoing treatment such as oxygen therapy or positive pressure treatment for conditions such as Obstructive Sleep Apnea (OSA) or Chronic Obstructive Pulmonary Disease (COPD) is often measured for safety and to enable controlling of the humidity delivered to the patient. Measurement of temperature near the patient is commonly performed using a probe inserted into the breathing tube, such as that of Fisher & Paykel Healthcare Limited, U.S. Pat. Nos. 6,272,933 and 6,584,972. Such a temperature probe is connected to the humidifier through a cable that runs external to the breathing circuit This approach has some drawbacks. In particular, the user must correctly install the temperature probe. If the probe is not correctly installed then the humidification system may malfunction which may increase risk to the patient. Existing end of breathing tube sensors require sensor wires to be run down the outside of the breathing tube. This lowers reliability of the sensors due to the vulnerability of these wires. Alternatively, if these wires are run down the inside of the breathing tube there would be an increase of the resistance to airflow and the hygiene of the breathing circuit would be lowered.

SUMMARY

It is an object of the present invention to provide a method of measuring properties of gases supplied to a patient that goes some way to overcoming the abovementioned disadvantages in the prior art or which will at least provide the industry with a useful choice.

Accordingly in a first aspect the present invention consists in an apparatus for measuring properties of gases being supplied to a patient comprising:

a gases supply, at least one delivery conduit including a heater wire for heating said conduit, wherein said heater wire is utilised in an electrical circuit to determine said properties of said gases.

Preferably said electrical circuit is connected in series with said heater wire and provides a measurement or enables a calculation of an indication of at least one of temperature, humidity, pressure and composition of said gases.

Preferably said electrical circuit is mounted and sealed on a printed circuit board that at least partially extends into the gases supplied to said patient through said at least one delivery conduit.

Preferably said electrical circuit is at least partially moulded into the wall of said delivery conduit.

Preferably said electrical circuit includes a sensing means with known properties at ambient temperature such that said sensing means can be matched with said at least one delivery conduit.

Preferably said sensing means is a temperature sensor.

Preferably said electrical circuit includes at least one measuring means in series with said heater wire.

Preferably said at least measuring means is a temperature measuring means.

Preferably said temperature measuring means includes a thermistor and diode in parallel and a reference resistor.

Preferably said thermistor and said diode are located at the end of said delivery conduit near to said patient and said reference resistor is included in said gases supply means.

Preferably said gases supply means includes a device to supply gas flow, such as a blower, and a humidifier to humidify said gases from said blower.

Preferably said gases supply means is a humidifier.

Preferably said electrical circuit includes a gases property measuring means.

Preferably said gases property measuring means includes at least one of a sensor, band pass filter or thermistor and at least one reference resistor.

Preferably said at least one of a sensor, band pass filter or thermistor are located at the end of said delivery conduit near to said patient and said at least one reference resistor and at least one band pass filter is included in said gases supply means.

The invention consists in the foregoing and also envisages constructions of which the following gives examples.

BRIEF DESCRIPTION OF THE DRAWINGS

Preferred forms of the present invention will now be described with reference to the accompanying drawings.

DETAILED DESCRIPTION

The present invention seeks to measure various properties, for example temperature or humidity, at the end of a gas delivery tube or conduit using sensors mounted on a wire, such as a wire used for heating the gases flow through the tube or conduit, where the wire resides within the delivery tube or conduit. A heated tube with a heating wire such as that described in Fisher & Paykel Healthcare Limited U.S. Pat. No. 6,078,730 or any other similar tube and heating wire could be utilised with the present invention.

Figure 1:
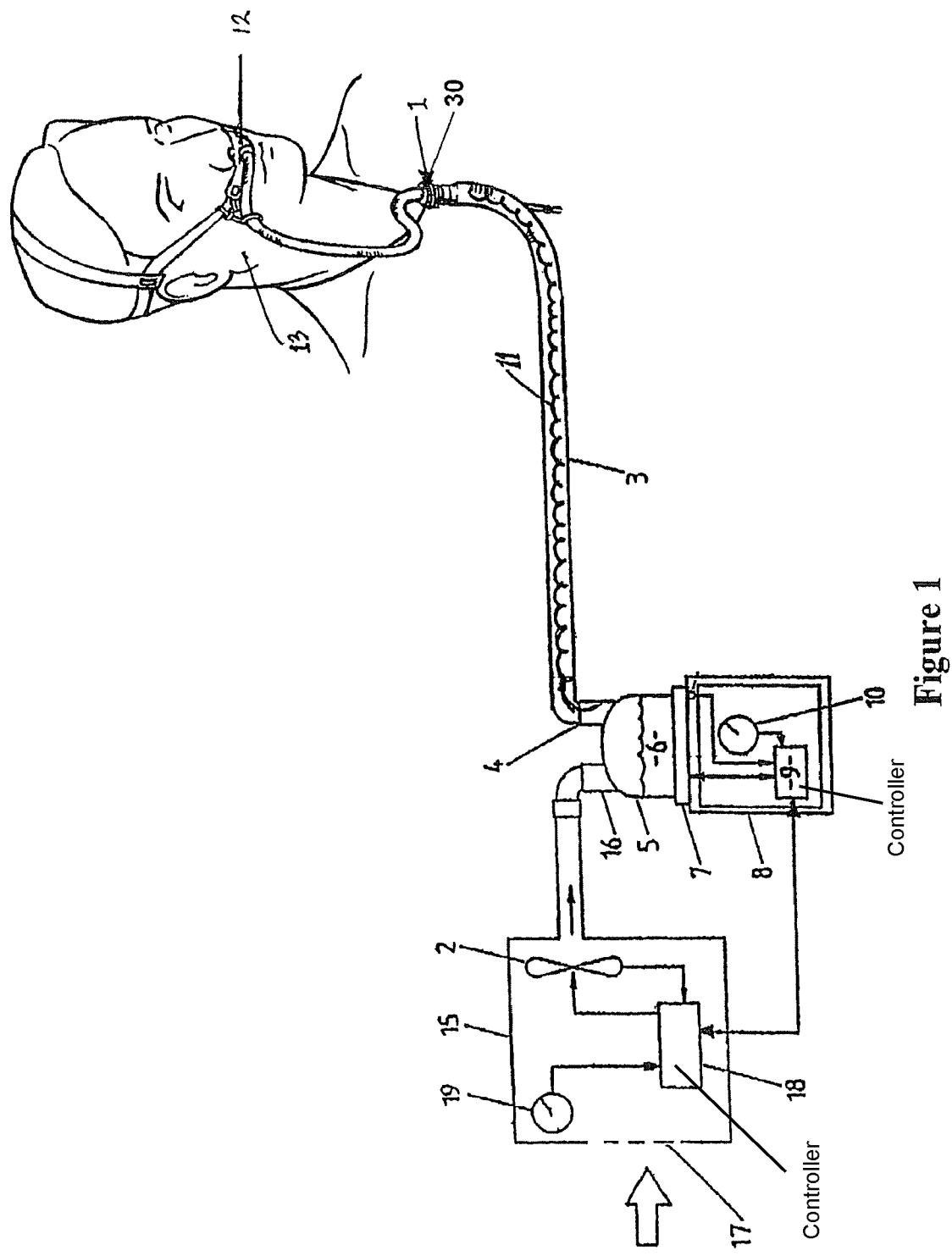
FIG. 1 is an illustration of a respiratory humidifier system that may be used with the method of the present invention of measuring temperature of gases supplied to a patient.

Referring to FIG. 1 a ventilation and humidifying system as might be used with the present invention is shown. A patient 13 is receiving humidified and pressurised gases through a nasal cannula 12 connected to a humidified gases transportation pathway or inspiratory conduit 3 that in turn is connected to a humidifier 8 (including humidification chamber 5) supplied with gases from a blower 15 or other appropriate gases supply means.

The inspiratory conduit 3 is connected to the outlet 4 of the humidification chamber 5 that contains a volume of water 6. The humidification chamber 5 is preferably formed from a plastics material and may have a highly heat conductive base (for example an aluminium base) that is in direct contact with a heater plate 7 of humidifier 8. The humidifier 8 is provided with control means or an electronic controller 9 that may comprise a microprocessor based controller executing computer software commands stored in associated memory. Gases flowing through the inspiratory conduit 3 are passed to the patient by way of the nasal cannula 12, but may also be passed to the patient by way of other patient interfaces such as a nasal or full face mask.

The controller 9 receives input from sources such as user input means or dial 10 through which a user of the device may, for example, set a predetermined required value (preset value) of humidity or temperature of the gases supplied to patient 13. In response to the user set humidity or temperature value input via dial 10 and other possible inputs such as internal sensors that sense gases flow or temperature, or by parameters calculated in the controller, controller 9 determines when (or to what level) to energise heater plate 7 to heat the water 6 within humidification chamber 5. As the volume of water 6 within humidification chamber 5 is heated, water vapour begins to fill the volume of the chamber above the surface of the water and is passed out of the humidification chamber 5 outlet 4 with the flow of gases (for example air) provided from a gases supply means or blower 15 which enters the humidification chamber 5 through inlet 16.

The blower 15 may be provided with a variable speed pump or fan 2 which draws air or other gases through the blower inlet 17. The speed of the variable speed pump or fan 2 maybe controlled by a further control means or electronic controller 18 which responds either to inputs from controller 9 or to user-set predetermined required values (preset values) of pressure or fan speed, via dial 19. Alternatively, the function of this controller 18 can be combined with the other controller 9.

A heating element or wire 11 is preferably provided within, around and throughout the conduit or tubing 3 to help prevent condensation of the humidified gases within the conduit. Such condensation is due to the temperature of the walls of the conduit being close to the ambient temperature, (being the temperature of the surrounding atmosphere) which is usually lower than the temperature of the humidified gases within the conduit. The heater element effectively replaces the energy lost from the gases through conduction and convection during transit through the conduit. Thus the conduit heater element ensures the gases delivered are at an optimal temperature and humidity.

Such a heater wire is commonly driven either with direct current (DC) or alternating current (AC) and in both cases the heating voltage is usually switched on and off to control the power applied to the heating element. In the present invention the heating element 11, which is most preferably a wire, is used along with an electronic circuit to determine properties of the gases supplied to the patient. The circuit (20 or 40 in FIGS. 2 and 3) is preferably connected in series with the heater wire 11. The circuit may be on a printed circuit board, or wired within a housing that may be a plastic moulding in the gases flow, or a circuit board that is at least partially moulded within the wall of the conduit or tubing 3. The properties that may be measured include temperature, pressure, gas composition and humidity. Two embodiments of the present invention are described below, one that operates using only a DC heating voltage and the other that can operate with a DC or AC heating voltage.

DC Heating Voltage

Figure 2:
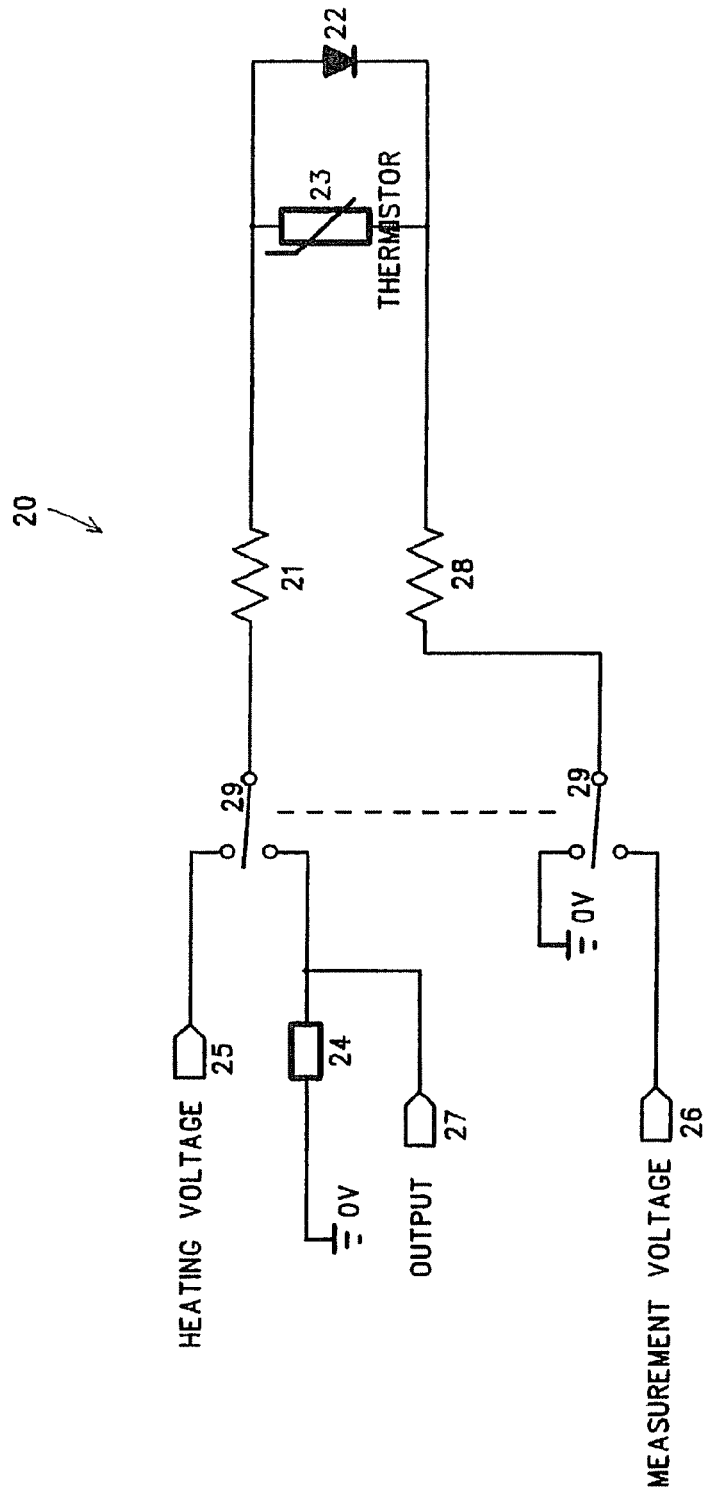
FIG. 2 is a circuit diagram of the electronics enabling the measurement of the temperature of gases to a patient, where the circuit is utilised when the system of the present invention is utilising DC heating and measuring voltages.

FIG. 2 shows a circuit 20 that may be utilised for carrying out the method of measuring temperature of the present invention. When a DC heating voltage 25 is applied to the heater wire the diode 22 conducts and current flows through the heater wire 21, 28 and the heater wire functions as normal and provides heating to the delivery tube 3. When the heating voltage 25 is switched off using switch 29, a measurement voltage 26, which has opposite polarity to the heating voltage 25 is applied to the heater wire. In this case, the current in the heater wire 21, 28 does not flow through the diode 22 but flows through the thermistor 23 and through a reference resistor 24. The voltage across the reference resistor 24 can then be measured at the output 27 and the temperature of the gases determined. The voltage measurement 27 across the reference resistor, 24, is converted to a temperature using a look up table or an equation to calculate a value for temperature. This is similar to a commonly used technique where the thermistor 23 forms a potential divider with the reference resistor 24.

More generally, the thermistor may be replaced by an impedance (for example, a resistor and a capacitive sensor) for pressure or humidity measurement. Either the impedance can be measured by measuring the voltage across the reference resistor 24 or the rise-time could be determined by looking at the voltage across the reference resistor 24 in time.

Figure 4:
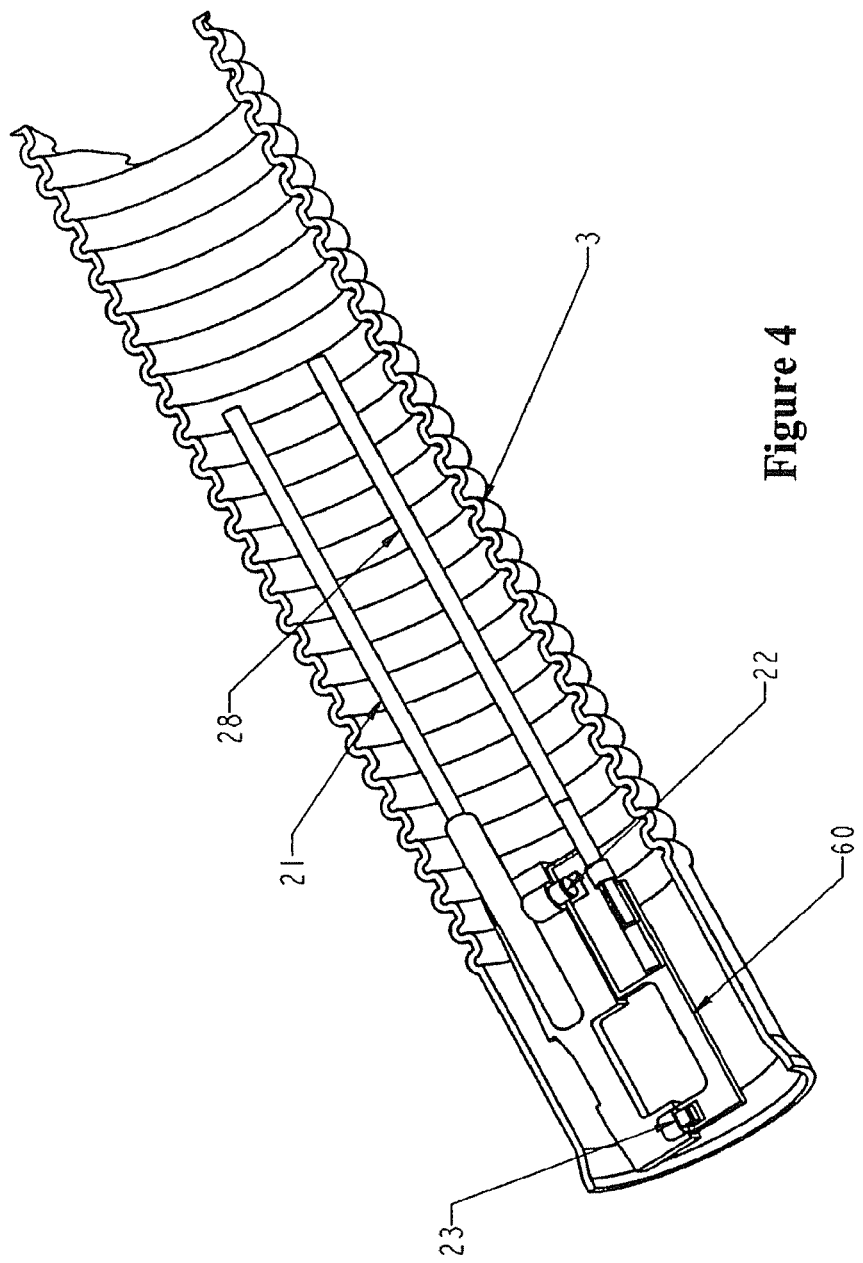
FIG. 4 is a cut away of a conduit including a circuit of the present invention on a printed circuit board and residing with the conduit in the area of gases flow.

Part of the circuit 20 would be included in the delivery conduit 3 and in particular the diode 22 and thermistor 23 (in parallel with one another) are preferably placed in series with the heater wire 21, 28 at a point in the heater wire at or near the end 30 (nearest the user 13, see FIGS. 1, 2 and 4) of the delivery tube 3, for example they may be interconnected on a printed circuit board, overmoulded with plastic for sealing and mounted in the gases stream through the delivery conduit as shown in FIG. 4. Furthermore, the circuit may be formed by interconnected parts in a housing, for example, a plastic housing, that protrudes from the plastic wall of the delivery tube into the gases flow through the conduit, in order to measure that gases properties. All other parts of the circuit 20 including the reference resistor 24 and the switching circuitry 29 would be included in the control circuitry of the humidifier 8.

The thermistor's value can be chosen to have different resistance curves with known properties at ambient temperature. The choice of a particular thermistor value for use with the circuit allows identification by the control system of the present invention and matching of that thermistor value with a specific conduit or tubing 3. Such that different thermistor values can be matched with a particular and appropriate conduit types and upon connection of the conduit to a humidifier or blower device, the control system can identify that thermistor and apply the appropriate control strategy to the heating of the conduit.

AC or DC Heating Voltage

Figure 3:
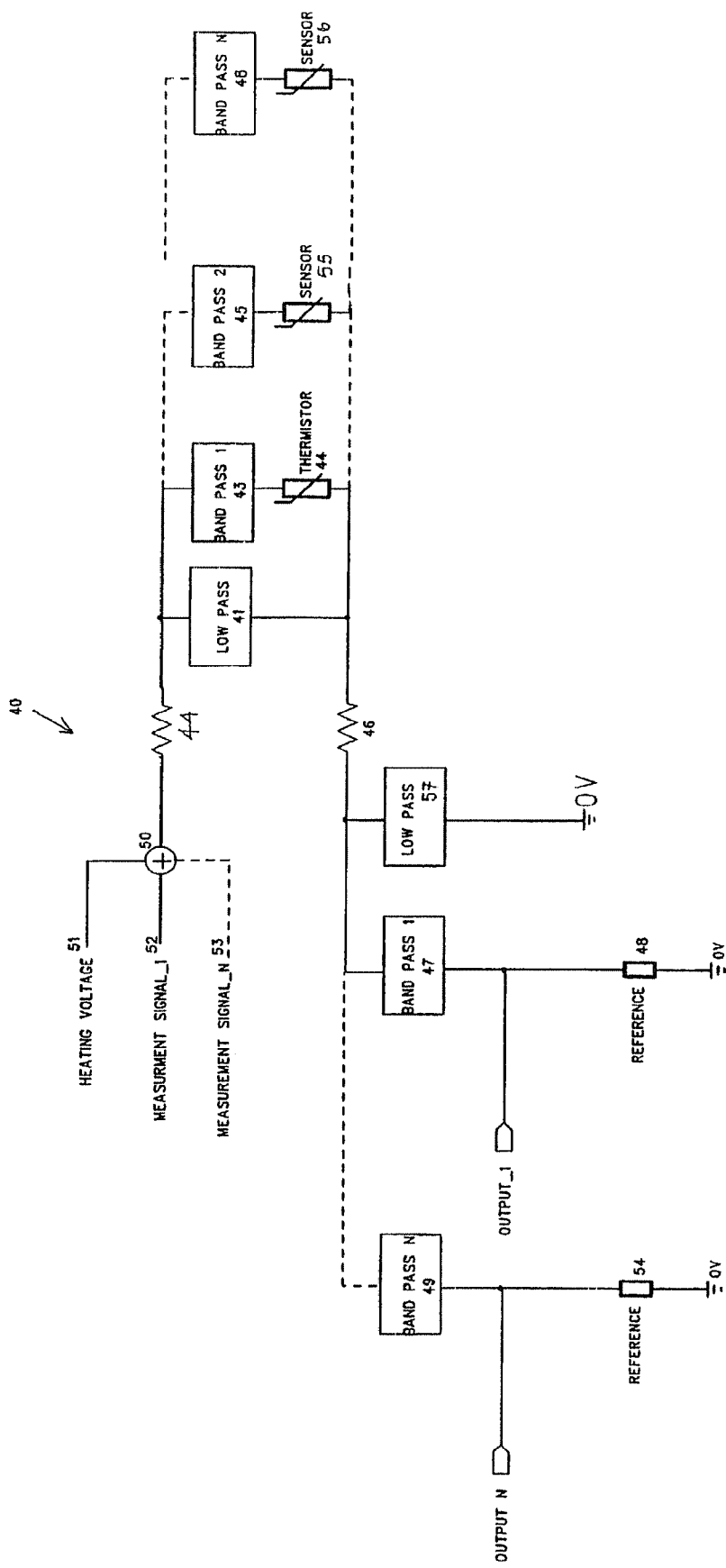
FIG. 3 is a circuit diagram of the electronics enabling the measurement of the temperature of gases to a patient, where the circuit is utilised when the system of the present invention is utilising DC or AC voltages for the heating and signal voltages.

The circuit shown in FIG. 2 is intended to be used when a DC heating voltage is used in conjunction with the heater wire, delivery conduit and system as shown in FIG. 1. An alternative embodiment of a circuit 40 that would provide measurement of the gases properties, such as temperature and is suitable for AC and DC voltages, is shown in FIG. 3. A number of voltage signals 51, 52, 53, which are at different frequencies, are added together at an adder 50. These signals include at least one heating signal 51 and at least one measuring signal 53. The combination of these signals passes down the heater wire 44, creating currents (heating and measuring) in the heater wire 44. A number of parallel paths are established 41, 43, 45 each containing a filter (for example, as shown in FIG. 3, one low pass filter 41 and three band pass filters 43, 45, 48) that each pass a different frequency range. These parallel paths (that is, filters, thermistors and/or sensors) are preferably located at the end 30 of the delivery tube 3, in a similar manner as described in relation to FIG. 2. The parallel paths allow the heating current to be passed through a different path to the measurement currents. It also allows multiple measurement signals to be passed through the heater wire so that different properties of the gases (e.g. temperature, pressure, humidity, composition) may be measured.

The heating and measurement currents return through the heater wire 46 and can be filtered through a number of measurement filters 47, 49, 57 in parallel that pass frequency bands that correspond to the filters, 41, 43, 45 located at the end 30 of the tube 3. The heating current takes a different path than the measurement currents. The measurement currents each take a different path depending on their frequency and this allows each measurement current to be measured by passing it through a reference resistor 48, 54 or similar. Again a look up table or equation may be used to convert the voltage across the reference resistor 48, 54 to, for example, a temperature. In the preferred embodiment of the present invention the measurement filters 47, 49, 57 would be included in the humidifier 8 control circuitry.

In a further embodiment one or more of the sensing elements 55, 56 at the end 30 of the delivery tube 3 could be replaced by a fixed impedance to allow identification of the tube so that different control algorithms can be used for different conduits or tubes.

FIG. 4 shows a cutaway view of a conduit 3 with a printed circuit board 60 housing the parts to one of the circuits of the present invention described above with reference to FIG. 2 or 3. The circuit board 60 is connected to the heating wires 21, 28 and as such is positioned within the conduit 3. In this manner, the thermistor 23 included on the board 60 is exposed to the gases flowing through the conduit 3 and can provide measurements of the properties of the gases.

The circuits and method of the present invention can be applied to a number of applications of these technologies for humidification and breathing circuit products. For example, the measurement of the temperature or humidity at the end of the delivery tube (or in a patient interface, for example, nasal cannula or mask) can be used to better control the humidifier, such that a more accurate temperature of gases can be supplied to the patient, providing optimal patient comfort and therapy. Additionally, other gases properties may be measured, such as the gases pressure or gas composition near the patient.

The apparatus of the present invention eliminates the need for external wires for sensing gases properties, as is required by the prior art. Furthermore the apparatus of the present invention only uses two pins or contacts (as opposed to four pins as used in current heated tube implementations). This means the system of the present invention is likely to be more reliable as the contacts/pins are likely to be less prone to breakage. The utilisation of the heater wire for measuring gases properties may also reduce the cost of the breathing tube 3 and associated parts, especially if the breathing tube is to be disposable.

What is claimed is:

1. A respiratory therapy system configured to provide respiratory gases to a COPD patient, the respiratory therapy system comprising:
   a blower comprising a fan;
   a humidifier in fluid communication with the blower to receive a flow of gases from the blower and the humidifier configured to humidify the flow of gases, the humidifier comprising:
      a heater plate; and
      a humidification chamber, the humidification chamber formed from a plastics material and including a heat conductive base of a different material that is configured to be positioned in direct contact with the heater plate;
      the heater plate configured to heat water within the humidification chamber to generate water vapour that is passed to the flow of gases from the blower to humidify the flow of gases;
   wherein the flow of gases comprises a proportion of oxygen;
   a controller configured to control the heater plate and determine when or to what level to energize the heater plate to heat the water in the humidification chamber based, at least in part, on a predetermined value of humidity of temperature based on input from a user via a user interface; the controller further configured to control operation of the blower to a user set value of fan speed or pressure based on an input from the user via the user interface;
   a gases outlet in fluid communication with the blower, the gases outlet configured to receive a flow of humidified gases from the humidification chamber, the gases outlet further comprising a plurality of electrical contacts;
   a delivery conduit configured to convey the flow of gases to a patient;
   a nasal cannula removably connectable to the delivery conduit, wherein the flow of gases are passed to the patient from the delivery conduit by way of the nasal cannula;
   the delivery conduit comprising:
      a wall defining a lumen, a proximal end and a distal end, the proximal end being closer to the patient;
      a heater wire configured to heat the flow of gases passing though the delivery conduit;
      an electrical circuit configured to provide an indication of at least one property of the flow of gases, wherein the heater wire forms part of the electrical circuit, and wherein the controller is configured to determine at least one property of the flow of gases using the indication from the electrical circuit;
      the electrical circuit includes a gases property sensor configured to sense a property of the flow of gases within the delivery conduit and other interconnected parts;
      the electrical circuit including the sensor at least partially being overmoulded for sealing and the overmoulding extending into a region of the flow of gases within conduit;

wherein the delivery conduit is configured to removably connect to the gases outlet and receive power from the gases outlet and provide measurement signals from the electrical circuit to the gases outlet via electrical contacts.

2. The system of claim 1, wherein the heater wire is within, around and throughout the delivery conduit.

3. The system of claim 1, wherein the electrical circuit is at least partially overmoulded into a wall of the delivery conduit.

4. The system of claim 1, wherein the electrical circuit includes a sensor with known properties at ambient temperature such that the controller can match the known properties of the sensor with at least one known type of delivery conduit for automatic delivery conduit identification purposes.

5. The system of claim 1, wherein the electrical circuit includes at least one sensor in series with the heater wire.

6. The system of claim 1, further comprising a gases outlet, wherein the humidifier is in fluid communication with the gases outlet and humidifier provides humidified gases to the gases outlet, the gases outlet further comprising electrical contacts, wherein the delivery conduit is configured to removably connect to the gases outlet and receive power from the gases outlet and provide a measurement signal to the gases outlet using less than four electrical contacts.

7. The system of claim 1, wherein the electrical circuit comprises a sensor and the sensor is located near a nasal cannula end of the delivery conduit.

8. The system of claim 1, wherein the overmoulding is plastic and forms a housing protecting the electrical circuit.

9. The system of claim 1, wherein the gases outlet comprises two electrical contacts and the delivery conduit comprises two electrical contacts that correspond to and connect to the electrical contacts on the gases outlet.

10. A system which provides a stream of heated and humidified gas to a patient through a nasal cannula, the system comprising:
   a controller;
   a blower;
   a humidifier;
   a nasal cannula;
   at least one delivery conduit removably connectable between the nasal cannula and the humidifier, the delivery conduit is configured to deliver heated and humidified gas to the nasal cannula for administration to a user, the delivery conduit including a heater wire for heating the stream of gas within the delivery conduit, the heater wire extending from at or near a first end of the delivery conduit to at or near a second end of the delivery conduit;
   a sensor configured to provide an indication of at least one property of the stream of gases, wherein the sensor is included as part of an electrical circuit including the heater wire, and wherein the controller is configured to determine the at least one property of the stream of gases using the indication from the sensor; and
   a moulding enclosing at least part of the sensor, the moulding extending into a region conveying the stream of gases through the delivery conduit.

11. The system of claim 10, wherein the heater wire is within, around and throughout the delivery conduit.

12. The system of claim 10, wherein the electrical circuit is at least partially positioned on a circuit board, and wherein the moulding encloses at least part of the circuit board and the at least partially moulding-enclosed circuit board at least partially extends into the gases supplied to the patient through the delivery conduit.

13. The system of claim 10, wherein the sensor is at least partially moulded into a wall of the delivery conduit and the moulding is a plastic overmoulding.

14. The system of claim 10, wherein sensor has known properties at ambient temperature such that the controller can match the known properties of the sensor with at least one known type of delivery conduit for automatic delivery conduit identification purposes.

15. The system of claim 10, wherein the sensor is in series with the heater wire.

16. The system of claim 10, wherein the sensor comprises a thermistor.

17. The system of claim 10, wherein the sensor is located near the second end of the delivery conduit which is nearest the nasal cannula.

18. The system of claim 10, further comprising an oxygen source.

19. The system of claim 10, wherein the moulding forms a housing.

20. The system of claim 10, wherein the humidifier comprises a humidification chamber and a heater plate, the humidification chamber being formed at least partially from a plastic material and having a highly conductive base of a different material that is positioned in direct contact with the heater plate when the chamber is in an operative position.

21. The system of claim 10, wherein the controller comprises one or more controllers configured to control operation of the blower to a user set value of fan speed or pressure based on an input from a dial.

22. The system of claim 10, wherein the system includes a gases outlet, wherein the humidifier is in fluid communication with the gases outlet and humidifier provides humidified gases to the gases outlet, the gases outlet further comprising electrical contacts, wherein the delivery conduit is configured to removably connect to the gases outlet and receive power from the gases outlet and provide a measurement signal to the gases outlet using less than four electrical contacts.

23. The system of claim 22, wherein the gases outlet comprises at least two electrical contacts and the delivery conduit comprises at least two electrical contacts that correspond to and connect to the electrical contacts on the gases outlet.

24. The system of claim 10, wherein the controller is configured to provide a gases flow at a preset flow rate for treatment of COPD.

25. A respiratory therapy system configured to provide respiratory gases to a COPD patient, the respiratory therapy system comprising:
   a blower comprising a fan;
   a humidifier in fluid communication with the blower and configured to receive a flow of gases from the blower and the humidifier configured to humidify the flow of gases, the humidifier comprising:
      a heater plate; and
      a humidification chamber, the chamber formed at least partially from a plastics material and including a heat conductive base formed of a different material that is configured to be positioned in direct contact with the heater plate,
      the heater plate configured to heat water within the humidification chamber to generate water vapour that is passed to the flow of gases from the blower to humidify the flow of gases;

wherein the flow of gases comprises a proportion of oxygen;

a controller configured to control the humidifier and the blower;

a gases outlet in fluid communication with the blower, the gases outlet configured to receive a flow of humidified gases from the humidification chamber, the gases outlet further comprising at least two electrical contacts;

a delivery conduit configured to convey the flow of gases to the patient; and a nasal cannula removably connectable to the delivery conduit, wherein the flow of gases are passed to the patient from the delivery conduit by way of the nasal cannula;

the delivery conduit further comprising:
- a wall defining a lumen, a proximal end and a distal end, the proximal end being closer to the patient;
- a heater wire configured to heat the flow of gases passing though the delivery conduit; and
- an electrical circuit connected to the heater wire, the electrical circuit configured to provide a signal to a controller through the heater wire indicative of at least one property of the flow of gases, the controller configured to determine the at least one property of the flow of gases;
- the electrical circuit including a gases property sensor to sense a property of the flow of gases within the delivery conduit and other interconnected parts, wherein the electrical circuit including the sensor is positioned in a plastic housing, and the plastic housing protruding from the wall of the delivery conduit and extending into the flow of gases within conduit;

wherein the delivery conduit is configured to removably connect to the gases outlet and receive power from the gases outlet and provide measurement signals from the electrical circuit to the gases outlet via the electrical contacts.

26. The system of claim 25, wherein the heater wire is within, around and throughout the delivery conduit.

27. The system of claim 25 wherein the sensor in series with the heater wire.

28. The system of claim 25 wherein the sensor comprises a thermistor.

* * * * *